United States Patent [19]
Bieringer et al.

[11] Patent Number: 6,159,900
[45] Date of Patent: *Dec. 12, 2000

[54] SYNERGISTIC HERBICIDAL AGENTS

[75] Inventors: Hermann Bieringer, Eppstein/Taunus; Erwin Hacker, Hochheim am Main; Rudolf Heinrich, Kelkheim/Taunus; Hans-Philipp Huff, Eppstein/Taunus; Jean Kocur, Hofheim am Taunus, all of Germany

[73] Assignee: Hoechst Aktiengesellschaft, Frankfurt am Main, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 07/759,478

[22] Filed: Sep. 13, 1991

[30] Foreign Application Priority Data

Sep. 15, 1990 [DE] Germany ............... 40 29 304

[51] Int. Cl.$^7$ ............... A01N 25/30; A01N 43/40; A01N 43/60; A01N 57/02
[52] U.S. Cl. ............... 504/206; 504/235; 504/250; 504/363
[58] Field of Search ............... 71/88, DIG. 1; 504/116, 270, 235, 250, 206, 363

[56] References Cited

U.S. PATENT DOCUMENTS

| | | | |
|---|---|---|---|
| 3,799,758 | 3/1974 | Franz | 504/206 |
| 4,140,513 | 2/1979 | Prill | 504/206 |
| 4,315,765 | 2/1982 | Large | 504/206 |
| 4,400,196 | 8/1983 | Albrecht et al. | 504/206 |
| 4,870,103 | 9/1989 | Röechling et al. | 71/88 |

FOREIGN PATENT DOCUMENTS

| | | |
|---|---|---|
| B-60925/90 | 2/1990 | Australia . |
| B-48333/90 | 8/1990 | Australia . |
| B-75480/81 | 9/1990 | Australia . |
| B-81718/91 | 2/1992 | Australia . |
| 0048436 | 3/1982 | European Pat. Off. . |
| 0 206 537 | 12/1986 | European Pat. Off. . |
| 0 255 760 | 2/1988 | European Pat. Off. . |
| 0255760 | 2/1988 | European Pat. Off. . |
| 0 290 416 | 11/1988 | European Pat. Off. . |
| 0336151 | 10/1989 | European Pat. Off. . |
| 0 356 812 A3 | 3/1990 | European Pat. Off. . |
| 0356812 | 3/1990 | European Pat. Off. . |
| 0402770 | 12/1990 | European Pat. Off. . |
| 0407874 | 1/1991 | European Pat. Off. . |
| 407874 | 1/1991 | European Pat. Off. . |
| 413267 | 2/1991 | European Pat. Off. . |
| 61-17029 | 8/1987 | Japan . |
| WO91/07089 | 5/1991 | WIPO . |

OTHER PUBLICATIONS

*Weed Science*, vol. 25 (1977) by Wyrill & Burnside, p. 275–287.
"The Herbicide Glyphosphate", by Turner (1985), pp. 221–240, Grossbard editor, Butterworths, London.
Proc. EWRS Symposium, "Factors Effecting Herbicidal Activity and Selectivity" (1988), pp. 227–232 Langelüddeke et al.
"McCutcheon's Emulsifiers and Detergents", International Edition (1988), p. 69.
Chemical Patents Index, Basic Abstracts Journal, Section Ch, Week 8705, Derwent Publications, 87–032875 (1987).

*Primary Examiner*—S. Mark Clardy
*Attorney, Agent, or Firm*—Frommer Lawrence & Haug

[57] ABSTRACT

When herbicides are applied, surfactants can affect the wettability of leaves of the plants and the effectiveness of the herbicides. According to the invention, a particular intensification of action is achieved when surfactants from the group comprising the $C_{10}$–$C_{18}$-alkyl polyglycol ether sulfates and their physiologically acceptable salts together with leaf-acting selective herbicides or the leaf-acting non-selective herbicides glyphosate, paraquat or diquat are applied.

16 Claims, No Drawings

SYNERGISTIC HERBICIDAL AGENTS

The invention relates to the technical field of plant protection agents, in particular combinations of active substance/surfactants, which are taken up via the green parts of the plant.

It is generally known that some herbicides reach the plants both via the leaves and via the roots, and other herbicides are taken up selectively, virtually only via the roots or only via the leaves. Thus, the herbicidal activity can depend to a decisive extent on whether the active substances can penetrate the plants rapidly and as completely as possible through the leaf tissue. In this context, surface-active substances play an important role, because in individual cases they can increase the wettability and act as a sort of slide on which the active substances penetrate the leaves.

It has now been found that the effectiveness of the herbicides is increased to a surprisingly great extent when certain herbicides are applied together with surfactants of the type of the alkyl polyglycol ether sulfates and their salts.

The invention relates to the use of surfactants from the group comprising the $C_{10}$–$C_{18}$-alkyl polyglycol ether sulfates and their physiologically acceptable salts as synergists for herbicides from the group comprising leaf-acting selective herbicides and the leaf-acting non-selective herbicides glyphosate, paraquat and diquat.

The surfactants to be used according to the invention are generally applied to the plants together with the herbicide, or the herbicides, or immediately in succession, preferably in the form of an aqueous spray mixture, which contains the surfactants and the herbicides in effective amounts, and, if appropriate, further customary auxiliaries.

The concentration of the surfactants to be used according to the invention in an aqueous spray mixture is, as a rule, from 0.05 to 2% by weight, preferably 0.1 to 1.0% by weight, in particular 0.1 to 0.3% by weight, of surfactant, based on detergent, a water application rate of 200 to 600 l/ha, in particular 300 to 400 l/ha, being preferred.

Examples of herbicides which can be used according to the invention are the following leaf-acting selective herbicides:

A) grass herbicides, for example

A 1) Herbicides of the type of the ($C_1$–$C_4$)alkyl, ($C_2$–$C_4$)-alkenyl and ($C_3$–$C_4$)-alkynyl phenoxyphenoxy-, benzylphenoxy- and heteroaryloxyphenoxycarboxylates, such as methyl 2-(4-(2,4-dichlorophenoxy)phenoxy)propionate (diclofop-methyl), methyl 2-(4-(4-bromo-2-chlorophenoxy)-phenoxy)propionate, methyl 2-(4-(4-trifluoromethyl-phenoxy)phenoxy)propionate, methyl 2-[4-(2-fluoro-4-trifluoromethylphenoxy)phenoxy]propionate, methyl 2-[4-(2-fluoro-4-bromophenoxy)phenoxy]propionate, methyl 2-(4-(2-chloro-4-trifluoromethylphenoxy)phenoxy)propionate, ethyl 4-(4-(4-trifluoromethylphenoxy)phenoxy)pent-2-enoate, methyl 2-(4-(2,4-dichlorobenzyl)phenoxy)propionate, ethyl 2-(4-(3,5-dichloropyridyl-2-oxy)phenoxy)propionate, propargyl 2-(4-(3,5-dichloropyridyl-2-oxy)-phenoxy)propionate, ethyl 2-[4-(5-difluoromethoxypyrid-2-yloxy)phenoxy] propionate, methyl 2-[4-(2-chloro-4-trifluoropyrid-2-yloxy) phenoxy]propionate (haloxyfop-methyl, Dowco 453), propargyl 2-[4-(4-chloro-6-fluoro-2-pyrid-1-yloxy)phenoxy] propionate (CGA 184 927), ethyl (R,S)-and(R)-2-(4-(6-chlorobenzoxazol-2-yloxy)phenoxy)-propionate (fenoxaprop-ethyl or fenoxaprop-P-ethyl), methyl 2-(4-(3-chloro-5-trifluoromethyl-2-pyridyloxy)-phenoxy) propionate, butyl (R,S)- and (R)-2-(4-(5-trifluoromethyl-2-pyridyloxy)phenoxy)propionate (fluazifop-butyl or fluazifop-P-butyl), methyl 2-(4-(3-fluoro-5-chloropyridyl-2-oxy)phenoxy)propionate, propargyl 2-(4-(3-fluoro-5-chloropyridyl-2-oxy)phenoxy)propionate, 2-(4-(6-chloro-2-quinoxalyloxy)phenoxy)propionic acid and its methyl ester and its ethyl ester (quizalofop, or quizalofop-methyl or -ethyl), methyl 2-(4-(6-fluoro-2-quinoxalyloxy)phenoxy) propionate, methyl 2-(4-(6-chloro-2-quinolyloxy)phenoxy) propionate, 5-methoxycarbonylmethyl 2-(4-(5-chloro-3-fluoropyridin-2-yloxy)phenoxy)thio-propionate, and other appropriate esters and amides such as 2-(propylidene-2-aminooxy)ethyl 2-[4-(6-chloro-2-quinoxalyloxy)phenoxy] propionate (propaquizafop, RO-17-3664), (±)-tetrahydrofurfuryl (2R)-2-[4-(6-chloroquinoxal-2-yloxy) phenoxy]propionate (UBI-C 4874), N-[2-[4-(3,5-dichloropyrid-2-yloxy)phenoxy]propionyl]isoxazolidine (isoxapyrifop); preferably herbicides of the phenoxyphenoxy- and heteroaryloxyphenoxypropionic acid type and their esters, A 2) cyclohexanedione derivatives, such as methyl 3-(1-allyloxyimino)butyl-4-hydroxy-6,6-dimethyl-2-oxocyclohex-3-enecarboxylate, 2-(N-ethoxybutyrimidoyl)-5-(2-ethylthiopropyl)-3-hydroxy-2-cyclohexen-1-one, 2-(N-ethoxybutyrimidoyl)-5-(2-phenylthiopropyl)-3-hydroxy-2-cyclohexen-1-one, 2-(1-allyloxyiminobutyl)-4-methoxycarbonyl-5,5-dimethyl-3-oxocyclohexenol, 2-(1-(3-chloroallyloxy)-iminopropyl)-5-(2-ethylthio)propyl)-3-hydroxycyclohex-2-enone (clethodim), 2-[1-[(E)-3-chloroallyloxyimino]-propyl]-5-(2-ethylthiopropyl)-3-hydroxycyclohex-2-enone (RE-45601), 2-(l-(ethoxyimino) butyl)-3-hydroxy-5-(thian-3-yl)cyclohex-2-enone (cycloxydim) or 2-(1-ethoxyiminopropyl)-5-(2,4,6-trimethylphenyl)-3-hydroxy-2-cyclohexen-1-one (tralkoxydim) and A 3) wild oat herbicides such as 1,2-dimethyl-3,5-diphenylpyrazolium salts (difenzoquat, difenzoquat-methylsulfate), N-benzoyl-N-(3,4-dichlorophenyl)-(D,L)-alanine and its ethyl ester (benzoylprop-ethyl), N-benzoyl-N-(3-chloro-4-fluorophenyl)alanine methyl ester and isopropyl ester (flamprop-M-methyl or flamprop-M-isopropyl); and also B) urea derivatives, for example 3-(4-isopropylphenyl)-1,1-dimethylurea (isoproturon), 3-(3-chloro-4-methyl)-1,1-dimethylurea (chlortoluron);

C) sulfonylurea herbicides, for example 1-(2-chlorophenylsulfonyl)-3-(4-methoxy-6-methyl-1,3,5-triazin-2-yl) urea (chlorsulfuron), 1-[(2-methoxycarbonylphenyl)-sulfonyl]-3-(4-methoxy-6-methyl-1,3,5-triazinyl-2-yl)urea (metsulfuron-methyl), 1-[(2-methoxycarbonylphenyl) sulfonyl]-3-methyl-3-(4-methoxy-6-methyl-1,3,5-triazin-2-yl)urea (DPX-L5300), 1-[(2-methoxycarbonylphenylmethyl)-sulfonyl]-3-(4,6-dimethoxypyrimid-2-yl)urea (bensulfuronmethyl), 1-[(2-methoxycarbonylphenyl)sulfonyl]-3-(di-methylpyrimid-2-yl)urea (sulfometuron-methyl), 1-[(2-methoxycarbonylthienyl)sulfonyl]-3-(4-methoxy-6-methyl-1,3,5-triazin-2-yl)urea (thiameturon-methyl), 1-[(2-ethoxycarbonylphenyl)sulfonyl]-3-(4-chloro-6-methoxypyrimid-2-yl)urea (chlorimuron-ethyl), 1-[(3-(N,N-dimethylaminocarbonyl)-pyrid-2-yl)sulfonyl]-3-(4,6-dimethoxypyrimid-2-yl)urea (nicosulfuron, SL 950), 1-[3-(ethylsulfonyl)-pyrid-2-yl)sulfonyl]-3-(4,6-dimethoxypyrimid-2-yl)urea (DPX-E9636), 1-[(2-(2-chloroethyl)-phenyl)sulfonyl]-3-(4-methoxy-6-methyl-1,3, 5-triazin-2-yl)urea (triasulfuron), 1-[(2-methoxycarbonylphenyl)-sulfonyl]-3-(4,6-bis-(difluoromethoxy)pyrimid-2-yl)urea (pirimisulfuron), 1-[(4-ethoxycarbonyl-1-methyl-1,2-imidazol-5-yl)-sulfonyl]-3-

(4,6-dimethoxypyrimid-2-yl)urea (pyrazosulfuron-methyl), 1-[(2-methoxycarbonylphenyl)sulfonyl]-3-(4-ethoxy-6-methylamino-1,3,5-triazin-2-yl)urea (DPX-A7881), cinosulfuron (CGA 142 464), 1-[(3-trifluoroethylpyrid-2-yl)sulfonyl]-3-(4,6-dimethoxypyrimid-2-yl)urea (flazasulfuron, SL 160), 1-[(N-methyl-N-methylsulfonylamino)sulfonyl]-3-(4,6-dimethoxypyrimid-2-yl)urea (amidosulfuron, Hoe 75032), 1-[(N-ethylsulfonyl-N-methylamino) sulfonyl]-3-(4,6-dimethoxypyrimid-2-yl)urea (SH-1), 1-[(N-ethyl-N-ethylsulfonylamino)sulfonyl]-3-(4,6-dimethoxypyrimid-2-yl)urea (SH-2),1-[(2-ethoxyphenoxy)sulfonyl]-3-(4,6-dimethoxypyrimid-2-yl)urea (SH-3), 1-[(N-(dimethylaminosulfonyl)-N-methylamino)sul-fonyl]-3-(4,6-dimethoxypyrimid-2-yl)urea (SH-4), D) diphenyl ether derivatives, for example 5-(2-chloro-4-trifluoromethylphenoxy)-2-nitro)-N-methylsulfonyl-benzamide (fomesafen), 5-(2-chloro-4-(trifluoromethyl)-phenoxy)-2-nitrobenzoic acid (acifluorfen, Na salt) and its carboxymethyl ester and carboxyethyl ester (fluoroglycofen-methyl, fluoroglycofen-ethyl), 2-chloro-6-nitro-3-phenoxyaniline (aclonifen), 1-(ethoxycarbonyl)ethyl 5-(2-chloro-4-trifluoromethylphenoxy)-2-nitrobenzoic acid (lactofen), 1-[5-(2-chloro-4-(trifluoromethyl)phenoxy)-2-nitrophenyl]-1-[N-(methoxycarbonylmethoxy)-imino]-2-methoxyethane (AKH-7088) and E) dicotyledon herbicides, for example hormone herbicides such as 2-(2,4-dichlorophenoxy)acetic acid (2,4-D), 2-(4-chloro-2-methylphenoxy)acetic acid (MCPA) and 2-(2-chloro-4-methylphenoxy)propionic acid (CMPP, mecoprop), 2,5-dichloro-6-methoxybenzoic acid (DICAMBA), hydroxy-benzonitrile herbicides, such as 3,5-dibromo-4-hydroxy-benzonitrile (bromoxynil) and 3,5-diiodo-4-hydroxybenzo-nitrile (ioxynil) and their salts and esters, for example the octanoates, and herbicides of various classes of structure, such as 3-[(methoxycarbonyl)aminophenyl] (3-methylphenyl)carbamate (phenmedipham), 2-(4-trifluoro-methylphenoxy)-3-(N-(2,5-difluorophenyl)aminocarbonyl1-pyridine (diflufenican), 4-amino-3,5-dichloro-2-fluoro-6-(carboxymethoxy)pyridine (fluroxypyr), 2-ethoxy-3,3-dimethyl-5-methanesulfonyloxy-2,3-dihydrobenzofuran (ethofumesate), 7-chloro-3-methylquinoline-8-carboxylic acid (quinmerac), 3,7-dichloroquinoline-8-carboxylic acid (quinchlorac), 3-isopropyl-1H-benzo-2,1,3-thiadiazin-4-one 2,2-dioxide (bentazone), 4-amino-3-methyl-6-phenyl-1,2,4-triazin-5(4H)one (metamitron), N-[4-chloro-2-fluoro-5-(1-methylprop-2-yn-1-yloxy)phenyl]-3,4,5,6-tetrahydrophthalimide (S-23121) and the N-phenylphthalimide derivative V-53482.

Other substances which can be employed in addition to the selective herbicides mentioned, of groups A to E, are also their enriched or pure optical forms if they exist and are herbicidally effective, and herbicides of analogous structure.

In addition, the leaf-acting non-selective herbicides N-phosphonomethylglycine (glyphosate), 1,1'-dimethyl-4,4,'-bipyridinium salts (paraquat) and 9,10-dihydro-8a, 10a-diazoniaphenanthrene salts (diquat) are also to be used according to the invention.

The herbicides which can be employed according to the invention are generally known. Most of them are described in "The Pesticide Manual", 8th Edition, British Crop Protection Council 1987 and in "Farm Chemicals Handbook '90", Meister Publishing Company, Willoughby, Ohio USA 1990, and the literature cited therein.

Some of the preferred herbicides, and herbicides which are not described in the above references, are listed in the following text:

Diclofop-methyl, i.e. methyl 2-[4-(2,4-dichlorophenoxy)-phenoxy]propionate, is a known herbicidal active substance which is employed for controlling annual grasses in cereals (see "The Pesticide Manual", 8th Ed. 1987, Brit. Crop Protection Council, p. 272).

UBI-C4874 belongs to the group of the heterocyclic phenoxy grass herbicides and is employed in a large number of dicotyledon crop plants for controlling annual and perennial grasses. It has the chemical name (±)tetrahydrofurfuryl (2R)-2-[4-(6-chloroquinoxalin-2-yloxy)phenoxy]propionate (see A. R. Bell et al., Brighton Crop. Protection Conference-Weeds-1989, pages 65–70).

Fenoxaprop-ethyl, i.e. ethyl 2-[4-(6-chlorobenzoxazol-2-yloxy)phenoxy)propionate is a known herbicide for controlling grasses in agricultural crops such as soya bean, sugar beet, potato, rice etc. It was first described in 1976 in DE-A-2,640,730; see also "The Pesticide Manual" 8th Edition, British Crop Protection Council 1987, page 379. It is employed in racemate form and currently also marketed as the D(+) isomer (common name: fenoxa-prop-P-ethyl) (see H. P. Huff et al., Brighton Crop Protection Conference-Weeds-1989, pp. 717–722). A combination of fenoxaprop-ethyl with the safener fenchlorazol-ethyl is also employed selectively against harmful plants in cereal crops such as rye and wheat (see H. Bieringer et al., Brighton Crop Protection Conference-Weeds-1989, pages 77–82 and H. Kbcher et al., loc. cit. pages 495–500).

RO-17–3664 (propaquizafop) is known from British Crop Protection Conf.-Weeds1987, p. 55 et seq. Isoxapyrifop is known from Brighton Crop Prot. Conf.-Weeds-1989, p. 59.

CGA 184 927 is known from Brighton Crop Prot. Conf.-Weeds-1989, p. 71 et seq.

Tralkoxydim is known from British Crop Prot. Conf.-Weeds-1987, p. 19 et seq.

RE-45601 is known from British Crop Prot. Conf.-Weeds-1987, p. 50 et seq.

Isoproturon, i.e. 3-(4-isopropylphenyl)-1,1-dimethylurea, is also a known herbicide which is employed for controlling grasses and cereals (cf. the above-cited "The Pesticide Manual", p. 491, 492).

Amidosulfuron, i.e. 3-(4,6-dimethoxypyrimidin-2-yl)-1-(N-methyl-N-(methylsulfonyl)aminosulfonyl)urea, is a herbicidal active substance for controlling broad-leaved weeds in cereals (cf. Z. Pfl. Krankh. Pfl. Schutz, Sonderheft XII, 489–497 (1990) and EP-A-0,131,258). SH-1 and SH-2 are structural analogs of amidosulfuron (see EP-A-0,131,258).

EP-A-0,342,569 discloses herbicidal 1-(2-alkoxyphenoxy-sulfonyl)-3-(pyrimid-2-yl)ureas which are particularly suitable for controlling dicotyledon weeds in cereals and which can be employed as herbicides according to the invention. From amongst these, particular mention must be made of the compound 3-(4,6-dimethoxypyrimidin-2-yl)-1-(2-ethoxyphenoxysulfonyl)urea (SH-3).

EP-A-0,347,788 discloses sulfonylureas for controlling monocotyledon and dicotyledon harmful plants in crops of useful plants. SH-4 is an example of herbicides of this type.

Pirimisulfuron (CGA 136 872) is known from Brighton Crop Prot. Conf.-Weeds-1987, p. 41–48. DPX-A 7881 is known from British Crop Prot. Conf.-Weeds-1987, p. 63 et seq. Cinosulfuron is known from "Agricultural Chemicals Book II, Herbicides", Thomson Publications, 1989–90, USA. Flazasulfuron is known from Y. Psujii et al., Abstr. Pap. Am. Chem. Soc. 195 MEET. AGRO. 10, 1988. Nicosulfuron (SL-950), i.e. 3-(4,6-dimethoxypyrimidin-2-yl)-1-(3-dimethylaminocarbonyl-pyridin-2-yl-sulfonyl)-urea, is a sulfonylurea herbicide which is employed for controlling grasses and broad-leaved weeds in maize (see F. Kimura et al. Brighton Crop Protection Conference-Weeds-1989, pages 29–34). DPX-E 9636 is known from Brighton Crop Prot. Conf.-Weeds-1989, p. 23 et seq. Fluoroglycofen is known from Brighton Crop Prot. Conf.-Weeds-1989, p. 47 et seq. AKH-7088 is known from Brighton Crop Prot. Conf.-Weeds-1989, p. 53 et seq. S-23121, i.e. N-[4-chloro-2-fluoro-5-(1-methylprop-2-yn-1-yloxy)phenyl]-3,4,5,6-tetrahydrophthalimide, is employed as a selective herbicide against broad-leaved harmful plants in cereals (see T. Hamada et al., Brit. Crop Prot. Conf-Weeds-1989, pages 41–46).

The N-phenyl-phthalimide derivatives also include V-53482, which is employed as a selective herbicide in rice and soya beans and in the "no-till" application in maize and soya beans (see Proceedings Southern Weed Science Meetings, Jan. 1990, USA).

The herbicides which are preferably selected are diclofop-methyl, UBI-C4874, fenoxaprop and its esters, in particular fenoxaprop-ethyl or fenoxaprop-P-ethyl, isoproturon, amidosulfuron, 1-(2-alkoxyphenoxysulfonyl)-3-pyrimid-2-ylurea herbicides, nicosulfuron, DPX-E9636, pirimisulfuron, Hoe 95404, metsulfuron-methyl, N-methyl-metsulfuron-methyl, (DPX-L5300), thiameturon-methyl, triasulfuron, phenmedipham, metamitron, quizalofop-ethyl, S-23212, V-53482 and bentazone as well as glyphosate.

The surface-active substances of the type of the $C_{10}$–$C_{18}$-alkyl polyglycol ether sulfates are preferably used in the form of their alkali metal salts such as sodium salts or potassium salts, and/or ammonium salts, but also in the form of magnesium salts, the polyglycol moiety preferably containing 2 to 5 ethylene oxide units. An example of a particularly preferred substance is sodium $C_{12}/C_{14}$-fatty alcohol diglycol ether sulfate (tradename ®Genapol LRO, Hoechst AG); in the following text, this substance will be referred to as wetting agent A.

The ratio by weight of herbicide to surfactant can vary within a wide range and depends on the effectiveness of the herbicide and on the concentration in the spray mixture. As a rule, it is in the range from 10:1 to 1:200, preferably 4:1 to 1:100.

It is already known that wetting agents of the type of the $C_{12}/C_{14}$-fatty alcohol diglycol ether sulfates can be used for reinforcing the action of glufosinate; cf. EP-A-048,436 (U.S. Pat. No. -4,400,196), EP-A-336,151, and Proc. EWRS Symp. Factors Affecting Herbicidal Activity and Selectivity, 227–232, 1988).

European Patent Application No. 90,112,739.9, which is not a prior publication, has already proposed to prepare aqueous preparations of herbicides from the group comprising glufosinate, fenoxaprop-P-ethyl, isoproturon and diclofop-methyl with Na-alkyl polyglycol ether sulfate (®Genapol LRO, Hoechst AG) and with defoamers from the group comprising the perfluoro-($C_6$–$C_8$)-alkylphosphinic acids and/or -phosphonic acids. More specifically, the defoamer used was a salt of a tallow fatty amine ethoxylate having 15 EO, i.e. 15 ethylene oxide units, (®Genamin T 150, Hoechst AG) and a defoamer of the abovementioned type, eFluowett PP, Hoechst AG.

German Patent Application P 3,938,564.7 has already proposed to prepare water-dispersible granules of fenoxaprop-ethyl or fenoxaprop-P-ethyl, these granules containing the 2- to 4-fold amount, relative to herbicide, of Genapol LRO as a wetting agent and a defoamer based on silicone, a dispersant based on a cresol/formaldehyde condensation product and an aluminum silicate.

The invention therefore also relates to herbicidal agents which contain a) herbicides from the group comprising leaf-acting selective herbicides and the leaf-acting non-selective herbicides glyphosate, paraquat and diquat, and b) surfactants from the group comprising the $C_{10-18}$-alkyl polyglycol ether sulfates and their physiologically acceptable salts, with the exception of aqueous preparations of herbicides from the group comprising fenoxaprop-P-ethyl, isoproturon and diclofop-methyl, which contain sodium $C_{12}$–$C_{14}$-alkyl diglycol ether sulfate in combination with a salt of tallow fatty amine ethoxylate having 15 EO and $C_6$–$C_{12}$-perfluoroalkylphosphinic acids/-phosphonic acids, and water-dispersible granules which contain fenoxaprop-ethyl or fenoxaprop-P-ethyl and sodium $C_{12}$–$C_{14}$-alkyl diglycol ether sulfate, defoamers based on silicone, dispersants based on cresol/formaldehyde condensation products and aluminum silicate.

Depending on the prevailing biological and/or chemiophysical parameters, the herbicidal agents according to the invention can be formulated in various ways. The following are examples of suitable possibilities for formulation: wettable powders (WP), water-soluble powders (SP), water-soluble concentrates, emulsifiable concentrates (EC), emulsions (EW) such as oil-in-water and water-in-oil emulsions, sprayable solutions or emulsions, suspension concentrates (SC), oil- or waterbased dispersions, oil-miscible solutions (OL), suspoemulsions, capsule suspensions (CS), dusts (DP), agents for seed-dressing, granules (GR) in the form of microgranules, spray granules, coated granules and adsorption granules, water-dispersible granules (WG), water-soluble granules (SG), ULV formulations, microcapsules and waxes.

These individual formulation types are known in principle and described, for example, in: Winnacker-Küchler, "Chemische Technologie" [Chemical Technology], Volume 7, C. Hauser Verlag Munich, 4th Ed. 1986; van Valkenburg, "Pesticides Formulations", Marcel Dekker N.Y., 2nd Ed. 1972–73; K. Martens, "Spray Drying Handbook, 3rd Ed. 1979, G. Goodwin Ltd. London.

The additionally required formulation auxiliaries such as inert materials, surfactants, solvents and further additives are equally known and described, for example, in: Watkins, "Handbook of Insecticide Dust Diluents and Carriers", 2nd Ed., Darland Books, Caldwell N.J.; H. v. Olphen, "Introduction to Clay Colloid Chemistry", 2nd Ed., J. Wiley & Sons, N.Y.; Marsden, "Solvents Guide", 2nd Ed., Interscience, N.Y. 1950; McCutcheon's "Detergents and Emulsifiers Annual, MC Publ. Corp., Ridgewood N.J.; Sisley and Wood, "Encyclopedia of Surface Active Agents", Chem. Publ. Co. Inc., N.Y. 1964; Schönfeldt, "Grenzfl ächenaktive Äthylenoxidaddukte" (Surface-active ethylene oxide adducts], Wiss. Verlags-gesell., Stuttgart 1976; Winnacker-Küchler, "Chemische Technologie" [Chemical Technology], Volume 7, C. Hauser Verlag Munich, 4th Ed. 1986.

Based on these formulations, combinations with other pesticidally active substances, fertilizers and/or growth regulators can also be prepared, for example in the form of a readymix or as a tank mix.

For further information with regard to the formulation of plant protection agents see, for example, G. C. Klingmann, "Weed Control as a Science", John Wiley and Sons, Inc., New York, 1961, pages 81–96, and J. D. Freyer, S. A. Evans, "Weed Control Handbook", 5th Ed., Blackwell Scientific Publications, Oxford, 1968, pages 101–103.

As a rule, the agrochemical preparations contain 0.1 to 99 percent by weight, in particular 0.1 to 95% by weight, of herbicidal active substance.

In wettable powders, the active substance concentration is, for example, about 10 to 90% by weight, the remainder to 100% by weight is composed of customary formulation components. In the case of emulsifiable concentrates, the active substance concentration can be about 1 to 80% by weight. Formulations in the form of dusts usually have a content of 1 to 20% by weight of active substance, sprayable solutions about 0.2 to 20% by weight. In the case of granules, the active substance content depends partly on whether the active compound is liquid or solid. The content of the water-dispersible granules is mostly between 10 and 90% by weight.

In addition, the active substance formulations mentioned may contain the adhesives, wetting agents, dispersants, emulsifiers, penetrants, solvents, fillers or carriers which are customary in each case.

In addition to the components a) and b) according to the invention, the herbicidal agents preferably also contain water and, if appropriate, organic solvents, and are formulated in the form of an aqueous concentrated dispersion or emulsion, or as a tank mix in the form of a dilute dispersion, emulsion or solution with a degree of dilution of up to that of the ready-for-use spray mixture. In concentrated aqueous dispersions or emulsions, the ratio by weight of herbicide a), in particular fenoxaprop-ethyl or fenoxaprop-P-ethyl, to surfactant b) is preferably from 1:1.5 to 1:4.

If desired, mixtures or mixed formulations with other active substances such as, for example, insecticides, acaricides, herbicides, safeners, fertilizers, growth regulators or fungicides, are also possible. Particularly preferred is a herbicidal agent, prepared in the form of a tank mix, which contains amounts of herbicide and surfactant which are preferred for use.

For use, concentrated formulations in commercially available form are, if appropriate, diluted in the customary manner, for example with water in the case of wettable powders, emulsifiable concentrates, dispersions and water-dispersible granules. Preparations in the form of dusts, spray granules and adsorption granules, sprayable solutions and spray mixtures prepared as a tank mix are customarily not diluted with other inert substances before use. However, it can be advantageous or necessary to add further amounts of surfactants b) according to the invention and/or other customary auxiliaries, in particular self-emulsifying oils or paraffin oils, to the spray mixtures. This is because the proportion of surfactants according to the invention cannot be increased at will in the case of some of the concentrated formulations without adversely affecting the stability of the formulation.

The application rate required of the active substances varies with the external conditions such as, inter alia, temperature, humidity and the nature of the herbicide used. It can vary within wide limits, for example between 0.001 and 10.0 kg/ha or more of active ingredient, but it is preferably between 0.005 and 5 kg/ha.

The noticeable improvement of action by the surfactants employed according to the invention such as, for example, wetting agent A, exceeds by far the performance of, for example, other conventional wetting agents and can therefore be referred to as being especially synergistically intensive. This is even more so since the surfactants according to the invention, by themselves, have no actual herbicidal activity and hardly damage the plant externally to a visible extent—occasionally, they result in slight brown discoloration (so-called "rusting") on the lamina of young plants, which, however, are outgrown very rapidly within a few days and are then no longer visible.

Wetting agent A on its own inflicts a slight growth shock on some sensitive young weeds, i.e. they show retarded growth compared with control plants for 1–2 weeks, but subsequently the plants recover and then show healthy growth.

However, when applied together with the herbicidal active substances, the surfactants according to the invention cause an extraordinarily powerful improvement of action, in such a way as that the active substances are taken up not only more rapidly, but also more completely, and can display their herbicidal effectiveness to a considerably greater extent.

Moreover, the effectiveness of the herbicides applied is much less adversely affected by climatic factors such as, for example, rain.

The invention therefore also relates to a method of controlling harmful plants, preferably for selectively controlling harmful plants, in crops of useful plants, which comprises applying a herbicidally effective amount of the herbicides a) mentioned in combination with at least one of the surfactants b) mentioned to the plants or the area on which they are grown.

A preferred meaning of harmful plants is the harmful plants which can already be controlled by the herbicides in question even without an added surfactant.

Naturally, the proportion of surfactant b) in concentrated formulations cannot be increased at will without adversely affecting the stability of the formulation. The ratio by weight of herbicide:surfactant in the concentrated formulations is preferably from 10:1 to 1:20.

On application, the ratio by weight of herbicide:surfactant is preferably in the range of 10:1 to 1:200, in particular 4:1 to 1:100, as a function of the effectiveness of the herbicide in question. At a water application rate of 200 to 600 l/ha, the concentration of surfactant b) according to the invention in the spray mixture is preferably 0.05 to 2% by weight, preferably 0.1 to 1.0% by weight, in particular 0.1 to 0.3% by weight, of detergent. A particularly preferred dosage rate is 300 to 900 g of detergent of the surfactant per ha of area under cultivation.

A) Biological Examples

Example A1

A range of economically important grass weeds were grown in sandy loam soil in the greenhouse in pots of diameter 13 cm, and, when they had reached a size and a growth stage as indicated in Table 1, treated with the herbicide fenoxaprop-P-ethyl on its own and in combination with wetting agent A. In this process, the formulation (see below) of the herbicide or of the tank mix of herbicide formulation, wetting agent and water, which had been diluted with water to give the spray mixture, was applied at a water application rate of 300 l/ha. As an additional comparison, the herbicide was applied in separate, analogous trials in combination with the conventional wetting agent isotridecanol hexaneethylene glycol ether (®Genapol X060, wetting agent B).

TABLE 1

Growth conditions and growth stages of the test plants

| Plant species | Greenhouse temp. day/night-time | Size (cm) | Growth stage |
|---|---|---|---|
| Alopecurus myosuroides (ALOMY) | 20/14° C. | 23–25 | tillering, middle |
| Avena fatua (AVEFA) | 20/14° C. | 31–33 | stem elongation, beginning |
| Sorghum halepense (SORHA) | 24–18° C. | 18–32 | 6-leaf stage |

4 weeks after the herbicides had been applied, the treated plants, which had been grown on in the greenhouse under the same temperature conditions, were assessed visually by determining the percentage damage to the plant growth.

These results are compiled in Table 2 below. From this table, it can be seen that wetting agent A increases the herbicidal activity of the herbicide fenoxaprop-P-ethyl, which was employed in the form of two conventional formulations, to a very considerable extent, while the conventional wetting agent B is not capable of such an action to the same extent.

TABLE 2

Herbicide damage to the test plants in %

| Active substance/ surfactant | g of AS/ha | AVEFA | ALOMY | SORHA |
|---|---|---|---|---|
| $H_1$ | 100 | 100 | 93 | 100 |
|  | 50 | 99 | 75 | 99 |
|  | 25 | 55 | 50 | 94 |
|  | 12 | 15 | 20 | 50 |
|  | 6 | — | — | 10 |
| $H_1$ + wetting agent A*) | 100 + 600 | 100 | 99 | 100 |
|  | 50 + 600 | 100 | 95 | 100 |
|  | 25 + 600 | 97 | 75 | 100 |
|  | 12 + 600 | 94 | 55 | 100 |
|  | 6 + 600 | — | — | 99 |
| $H_1$ + wetting agent B*) | 100 + 600 | 99 | 93 | 100 |
|  | 50 + 600 | 99 | 75 | 100 |
|  | 25 + 600 | 93 | 60 | 98 |
|  | 12 + 600 | 45 | 35 | 88 |
|  | 6 + 600 | — | — | 45 |
| $H_2$ | 100 | 100 | 97 | 100 |
|  | 50 | 99 | 85 | 100 |
|  | 25 | 83 | 45 | 99 |
|  | 12 | 15 | 25 | 90 |
|  | 6 | — | — | 60 |
| $H_2$ + wetting agent A*) | 100 + 600 | 100 | 99 | 100 |
|  | 50 + 600 | 100 | 97 | 100 |
|  | 25 + 600 | 99 | 88 | 100 |
|  | 12 + 600 | 99 | 83 | 100 |
|  | 6 + 600 | — | — | 99 |
| Wetting agent A*) | 600 | 0 | 0 | 0 |
| Wetting agent B*) | 600 | 0 | 0 | 0 |

Abbreviations in Table 2
AS = based on active substance (herbicide) or detergent (wetting agent)
$H_1$ = fenoxaprop-P-ethyl, formulated as a 7.5% strength EW (concentrated emulsion)
$H_2$ = fenoxaprop-P-ethyl, formulated as a 9% strength EC (ecmulsion concentration)
*) = at a water application rate of 300 l/ha, wetting agents were employed at a concentration of in each case 0.2% by weight of detergent in the spray water.
Wetting agent A = Na $C_{12}/C_{14}$-fatty alcohol diglycol ether sulfate (® Genapol LRO, 28% strength aqueous solution)
Wetting agent B = isotridecanol polyglycol ether having 6 EO (® Genapol X060)

Example A2

Wheat (TRZAS) and the harmful grasses wild oat (AVEFA) and slender foxtail (ALOMY) occurring in cereal crops were grown in the greenhouse at temperatures from 18° C./12° C. until they had reached the stage "tillering, middle", corresponding to a size of 24–28 cm, and treated with the preparations according to the invention.

The herbicide employed was fenoxaprop-P-ethyl together with the safener fenchlorazol-ethyl in a ratio of 2:1 ($H_3$).

Application and assessment were as described under Example A1. 4 weeks after the application, the herbicidal activities, which are compiled in Table 3 below, were measured.

TABLE 3

Control of harmful grasses in wheat

| Active substance/ surfactant | g of AS/ha | TRZAS | AVEFA | ALOMY |
|---|---|---|---|---|
| $H_3$ | 100 | 0 | 99 | 90 |
|  | 50 | 0 | 85 | 80 |
|  | 25 | 0 | 60 | 35 |
|  | 12 | 0 | 10 | 5 |
| $H_3$ + wetting agent A | 100 + 750 | 0 | 99 | 98 |
|  | 50 + 750 | 0 | 98 | 92 |
|  | 25 + 750 | 0 | 97 | 88 |
|  | 12 + 750 | 0 | 95 | 75 |
| $H_3$ + wetting agent B | 100 + 750 | 0 | 99 | 95 |
|  | 50 + 750 | 0 | 97 | 88 |
|  | 25 + 750 | 0 | 90 | 70 |
|  | 12 + 750 | 0 | 60 | 25 |
| Wetting agent A | 750 | 0 | 0 | 0 |
| Wetting agent B | 750 | 0 | 0 | 0 |

Abbreviations:
AS = active substance or detergent
$H_3$ = fenoxaprop-P-ethyl/fenchlorazol (2:1) in the form a 7.5% strength EW (7.5% strength aqueous emulsion)
Wetting agents A and B are as defined in Table 1 and were employed with 0.25% by weight of detergent in the spraying water, at a water application rate of 300 l/ha.

The results show that wetting agent A considerably increases the effectiveness of herbicide $H_3$, formulated as a 7.5% strength EW, when only 0.25% of wetting agent A was added to the spray mixture. The conventional wetting agent is not capable of provoking a similar synergistic effect.

Example A3

The intensification of the action of nicosulfuron (SL-950) by wetting agent A was tested analogously to Example A1. The results are compiled in Table 4:

TABLE 4

Herbicidal action of SL-950 (nicosulfuron) with ® Genapol LRO (wetting agent) added

| Active substance/ surfactant | Dosage rate in g of AS/ha | % Herbicidal activity against | | |
|---|---|---|---|---|
|  |  | AVEFA | STEME | MATCH |
| Nicosulfuron (in the form of WG 75) | 10 | 0 | 0 | 0 |
|  | 20 | 23 | 65 | 63 |
|  | 40 | 58 | 75 | 73 |
|  | 60 | 60 | 80 | 83 |
| Nicosulfuron WG 75 + wetting agent | 10 + 600 | 75 | 85 | 85 |
|  | 20 + 600 | 90 | 98 | 95 |
|  | 40 + 600 | 93 | 100 | 98 |
|  | 60 + 600 | 97 | 100 | 100 |
| Nicosulfuron (in the form of SC 04) | 10 | 35 | 70 | 65 |
|  | 20 | 63 | 90 | 80 |
|  | 40 | 78 | 100 | 95 |
|  | 60 | 94 | 100 | 97 |
| Nicosulfuron SC 04 + wetting agent | 10 + 600 | 70 | 98 | 85 |
|  | 20 + 600 | 90 | 100 | 100 |
|  | 40 + 600 | 95 | 100 | 100 |
|  | 60 + 600 | 100 | 100 | 100 |

Abbreviations:
AVEFA = *Avena fatua*
STEME = *Stellaria media*
MATCH = *Matricaria chamomilla*
Nicosulfuron WG 75 = nicosulfuron in the form of granules, 75% content
Nicosulfuron SC 04 = nicosulfuron in the form of a suspension concentrate, 4% content
Wetting agent = wetting agent A as in Table 1

Example A4

The action of UBI-C4874 in comparison with the combination of the herbicide with wetting agent A was tested analogously to Examples A1 to A3. The herbicide had been formulated as an emulsion concentrate EC 120 and was applied to the plants in the 3- to 4-leaf stage (beginning of tillering) at a water application rate of 300 1 per ha. The assessment was carried out 2 to 3 weeks after the application. The results are compiled in Table 5:

TABLE 5

Intensification of action of UBI-C4874

| g of AS/ha | % Action after 14–21 days against | | | |
|---|---|---|---|---|
| | ECHCO | ELEAF | SORVE | Soya bean |
| C 4874 60 | 50 | 96 | 43 | 0 |
| (in the 40 | 17 | 55 | 7 | 0 |
| form of 30 | 10 | 35 | 0 | 0 |
| EC 120) | | | | |
| C 4874 + 40 + 900 | 99 | 99 | 100 | 0 |
| wetting | | | | |
| agent A | | | | |
| Wetting 900 | 0 | 0 | 0 | 0 |
| agent A | | | | |

Abbreviations:
ECHCO = *Echinochloa colonun*
ELEAF = *Eleusine africana*
SORVE = *Sorghum verticiliflorum*
EC 120 = emulsifiable concentrate, 12% content
Wetting agent A = see Table 1; the concentration in the spray mixture was 0.3% by weight.

Example A5

Analogously to Example A1, the sulfonylurea DPX-E9636 in combination with wetting agent A was applied to dicotyledon weeds in stage 24 and the effect was assessed 5 weeks after the treatment (see Table 6):

TABLE 6

Intensification of action of DPX-9636

| Agent | Dosage rate in g of AS/ha | Action [%] against | |
|---|---|---|---|
| | | ABUTH | SEBEX |
| DPX-E9636 | 6.25 | 0 | 7 |
| (WP 20) | 12.5 | 0 | 17 |
| | 25.0 | 0 | 33 |
| DPX-E9636 + | 6.25 + 280 | 7 | 70 |
| wetting | 12.25 + 280 | 37 | 82 |
| agent A | 25.0 + 280 | 60 | 89 |

Abbreviations:
DPX-E9636 WP 20 = active substance in the form of a water-dispersible powder, 20% content
Wetting agent A = ® Genapol LRO, the concentration in the spray mixture was 1% by weight of detergent
ABUTH = *Abutylon theophrasti*
SEBEX = *Sesbania exaltata*

Example A6

Analogously to Examples A1 to A5, the intensification of action of pirimisulfuron by wetting agent A was tested for dicotyledon weeds, but in a field trial. The water application rate was 300 l/ha. Results (see Table 7)

TABLE 7

Intensification of action of pirimisulfuron

| Agent | Dosage rate in g of AS/ha | Action [%], 28 days after treatment | | |
|---|---|---|---|---|
| | | ABUTH | SEBEX | SIDSP |
| Pirimi- | 20 | 0 | 0 | 0 |
| sulfuron | 40 | 33 | 10 | 7 |
| (WG 75) | | | | |
| Pirimi- | 20 + 280 | 90 | 95 | 70 |
| sulfuron + | 40 + 280 | 93 | 97 | 88 |
| wetting | | | | |
| agent A | | | | |

Abbreviations:
WG 75 = water-dispersible granules, active substance content 75%
ABUTH = *Abutylon theophrasti*
SEBEX = *Sesbonia exaltata*
SIDSP = *Sida spinosa*

Example A7

Tests with the sulfonylureas (WP 20) and SH-3 (WP 20) as herbicide and with Galium aparine as the harmful plant were carried out analogously to Example A6 (see Table 8):

TABLE 8

| Agent | Dosage rate [g of AS/ha] | Action against *Galium aparine* |
|---|---|---|
| Amidosulfuron | 15 | 95 |
| | 30 | 97 |
| Amidosulfuron + wetting agent A | 15 + 280 | 97 |
| SH-3 | 15 | 88 |
| | 30 | 97 |
| SH-3 + wetting agent A | 15 + 280 | 97 |

Example A8

Analogously to Example A1, the sulfonylureas indicated in Table 9 were tested against Chenopodium album (CHEAL) and Galium aparine (GALAP):

TABLE 9

| Agent | Dosage rate [g of AS/ha] | CHEAL | GALAP |
|---|---|---|---|
| Metsulfuron-methyl (DF 20) | 4 | 27 | 68 |
| Metsulfuron-methyl + wetting agent A | 4 + 250 | 100 | 80 |
| Thiameturon-methyl (DF 75) | 40 | 85 | 88 |
| Thiameturon-methyl + wetting agent A | 40 + 250 | 93 | 95 |
| N-methyl-met-sulfuron-methyl (DF 75) | 10 | 85 | 23 |
| N-methyl-met-sulfuron-methyl + wetting agent | 10 + 250 | 100 | 65 |
| Triasulfuron | 10 | 63 | 90 |
| Triasulfuron + wetting agent A | 10 + 250 | 90 | 98 |

Example A9

Analogously to Example A1, weeds were treated with glyphosate or a combination of the herbicide with wetting agent A, with overhead irrigation being carried out 30 minutes after the application at a rate of 15 mm of water per m2, to determine rain fastness. As shown by the results in Table 10, the high activity of glyphosate is only retained in the test where a wetting agent is added.

TABLE 10

| Agent | Dosage rate in g of AS/ha | % action ANTAR | VIOAR | APESV |
|---|---|---|---|---|
| Glyphosate | 1440 | 0 | 0 | 0 |
| Glyphosate + wetting agent A*) | 1400 + 300 | 100 | 100 | 98 |

Notes:
*)The concentration of wetting agent A in the spray mixture was 0.1% by weight
APESV = *Apera spica venti*
ANTAR = *Anthemis arvense*

Example A10

The effect of the addition of various wetting agents on the action of glyphosate was tested in a container trial. For this purpose, spring wheat (Triticum aestivum, TRZAS), spring barley (Hordeum vulgare, HORVS) and spring oilseed rape (Brassica napus, BRSNS) were used as test plants, and these were sown in pots towards the end of June and placed in a vegetation shed with ambient conditions. Approximately 3 weeks after sowing, when the plants had reached the 4-leaf stage, the herbicide was sprayed onto the plants in the form of a commercially available formulation of the herbicide glyphosate with 360 g/l of acid equivalent in the form of its isopropylamine salt, using a water application rate of 300 l/ha. The wetting agent-containing spray mixtures contained wetting agent at a concentration of 0.2% by weight of detergent. After the treatment, the pots were replaced in the vegetation shed, and the damage was assessed after 2 weeks (results, see Table 11).

This test showed that the herbicide was generally good when used on its own at a dosage rate of 270 g/ha of active ingredient, but at half the dosage rate its effectiveness was only very incomplete. In contrast, the addition of wetting agent A at this dosage rate resulted in a complete destruction of all three test plants. In contrast, when the remaining wetting agents were used, the action was either not improved at all, or only to a very much smaller extent.

TABLE 11

| Acid equivalent of glyphosate in g/ha | % action TRZAS | HORVS | BRSNS |
|---|---|---|---|
| 1. Standard formulation without additive | | | |
| 135 | 58 | 0 | 53 |
| 270 | 100 | 99 | 99 |
| 540 | 100 | 100 | 100 |
| 2. Standard formulation plus wetting agent A | | | |
| 135 | 100 | 100 | 95 |
| 270 | 100 | 100 | 99 |
| 540 | 100 | 100 | 100 |
| 3. Standard formulation plus wetting agent B | | | |
| 135 | 65 | 45 | 30 |
| 270 | 99 | 73 | 40 |
| 540 | 100 | 100 | 80 |

TABLE 11-continued

| Acid equivalent of glyphosate in g/ha | % action TRZAS | HORVS | BRSNS |
|---|---|---|---|
| 4. Standard formulation plus wetting agent C | | | |
| 135 | 78 | 70 | 20 |
| 270 | 98 | 80 | 80 |
| 540 | 100 | 100 | 95 |
| 5. Standard formulation plus wetting agent D | | | |
| 135 | 88 | 95 | 30 |
| 270 | 100 | 100 | 99 |
| 540 | 100 | 100 | 100 |

Abbreviations:
Wetting agent A = sodium $C_{12}/C_{14}$-fatty alcohol diethylene glycol ether sulfate (® Genapol LRO)
Wetting agent B = ethoxylated isotridecanol having 6 EO (ethylene oxide units) (® Genapol X060, Hoechst)
Wetting agent C = oxalkylated polysiloxane (® Silwet L 77, Union Carbide)
Wetting agent D = ethoxylated tallow fatty amine having 20 EO (® Genamin T-200)

Example 11

Analogously to Example A1, the action of isoproturon in combination with wetting agent A against useful plants and harmful plants was tested in a container trial. Isoproturon was employed in two conventional formulations. The water application rate was 300 l/ha, and the concentration of wetting agent in the spray mixture was 0.25% by weight. The results are compiled in Table 12.

TABLE 12

| Agent | Dosage rate [g of AS/ha] | % action after 2 weeks against TRIAE | ALOMY | APSPV |
|---|---|---|---|---|
| Isoproturon | 1000 | 0 | 35 | 38 |
| WP 75 | 500 | 0 | 15 | 15 |
| (® Arelon WP | 250 | 0 | 5 | 0 |
| 75%) | 125 | 0 | 0 | 0 |
| | 63 | 0 | 0 | 0 |
| Isoproturon | 1000 + 750 | 0 | 55 | 95 |
| WP 75 + | 500 + 750 | 0 | 53 | 94 |
| wetting | 250 + 750 | 0 | 5 | 40 |
| agent A | 125 + 750 | 0 | 0 | 10 |
| | 63 + 750 | 0 | 0 | 0 |
| Isoproturon | 1000 | 0 | 0 | 68 |
| DIS 50 | 500 | 0 | 0 | 25 |
| (® Arelon DIS | 250 | 0 | 0 | 5 |
| 50%) | 125 | 0 | 0 | 0 |
| | 63 | 0 | 0 | 0 |
| Isoproturon | 1000 + 750 | 0 | 75 | 83 |
| DIS 50 + | 500 + 750 | 0 | 35 | 78 |
| wetting | 250 + 750 | 0 | 10 | 38 |
| agent A | 125 + 750 | 0 | 0 | 10 |
| | 63 + 750 | 0 | 0 | 0 |

Abbreviations:
TRIAE = Weizen (*Triticum aestivum*)
ALOMY = *Alopecurus myosuroides*
APSPV = *Apera spica-venti*
WP 75 = water-dispersible powder with 75% active substance content
DIS 50 = dispersion containing 50% of active substance Example A12

Analogously to Example A7, an emulsifiable concentrate of phenmedipham, wetting agent A and water was mixed in the form of a tank mix and employed in a field trial against dicotyledon harmful plants in the four-leaf stage (stage 22)

and in sugar beet, using a water application rate of 300 l/ha. 5 weeks after the treatment, the results shown in Table 13 were obtained.

TABLE 13

| Agent | Dosage rate [g of AI/ha] | % action in | | |
|---|---|---|---|---|
| | | LAMAM | ERUVE | BETVU |
| Phenmedipham | 628 | 42 | 35 | 0 |
| | 1363 | 78 | 85 | 0 |
| Phenmedipham + wetting agent A | 628 + 280 | 98 | 90 | 0 |

LAMAM = *Lamium amplexicaule*
ERUVE = *Eruca vesicaria*
BETVU = sugar beet (*Beta vulgaris*)

Example 13

Analogously to Example A12, metamitron (added to the tank mix in the form of water-dispersible granules, content 70%) and wetting agent A were tested against Papaver rhoeas (PAPRH) in a field trial (see Table 14):

TABLE 14

| Agent | Dosage rate [g of AI/ha] | % Action against PAPRH |
|---|---|---|
| Metamitron | 2.3 | 38 |
| | 3.5 | 63 |
| Metamitron + wetting agent A | 2.3 + 0.25 | 96 |

Example 14

Analogously to Example A12, quizalofop-ethyl, which was added to the tank mix in the form of a 10% emulsifiable concentrate, and wetting agent A were applied against Hordeum vulgare (HORVU) in the stage "beginning of stem elongation" and Setaria viridis (SETVI) at the beginning of tillering in a field trial at a water application rate of 300 l/ha. Hordeum vulgare in this context is not the crop plant barley, but spontaneously occurring barley ("volunteer barley"), which is a grass weed. The results are compiled in Table 15.

TABLE 15

| Agent | Dosage rate [g of AS/ha] | % action against | |
|---|---|---|---|
| | | HORVU | SETVI |
| Quizalofop-ethyl | 50 | 75 | 48 |
| | 75 | 87 | — |
| | 100 | 88 | — |
| Quizalofop-ethyl + wetting agent A | 50 + 140 | 87 | 95 |
| Quizalofop-ethyl + wetting agent A | 75 + 84 | 89 | — |
| Quizalofop-ethyl + wetting agent A | 75 + 250 | 91 | — |
| Quizalofop-ethyl + wetting agent A | 75 + 420 | 84 | — |

Example A15

Analogously to Example A14, bentazone, which was employed for the tank mix in the form of a 48% strength commercially available emulsifiable concentrate, and wetting agent A were tested in a field trial against Portulaca oleracea (POROL) and Cyperus rotundus (CYPRO). It can be seen from the results (see Table 16) that the addition of wetting agent A facilitates a considerable reduction of active substance, while maintaining the same action.

TABLE 16

| Agent | Dosage rate [g of AS/ha] | % action against | |
|---|---|---|---|
| | | POROL | CYPRO |
| Bentazone | 720 | 85 | 25 |
| " | 960 | 97 | 27 |
| " | 1440 | 100 | 50 |
| Bentazone + wetting agent A | 720 + 280 | 100 | 55 |

The following text gives examples of formulations according to the invention, without limiting the nature of the formulations according to the invention which are possible.

B) FORMULATION EXAMPLES

Example B1 (EW formulation)

9.0% by weight of fenoxaprop-P-ethyl are dissolved in 35.0% by weight of a mixture of aromatics (boiling range 219° C.–282° C.) and treated with 4.0% by weight of fatty acid polyglycol ester (having 40 EO). This mixture is added slowly at room temperature with stirring to 30.0% by weight of an aqueous solution of the potassium salt of a phosphorylated ethylene oxide/propylene oxide/ethylene oxide block copolymer, and the mixture is stirred until the emulsion is homogeneous. 15.0% by weight of the sodium salt of an alkyl polyglycol ether sulfate (wetting agent A) is then added, with further stirring, and then 7.0% by weight of glycerol, and stirring of the white emulsion which has formed is continued for another 15 minutes.

(Note: EO=ethylene oxide units —$CH_2CH_2O$—)

Example B2 (EW formulation)

6.0% by weight of fenoxaprop-P-ethyl and 3.0% by weight of fenchlorazol-ethyl are dissolved in 40% by weight of a mixture of aromatics (boiling range 219° C.–282° C.) and treated with 4.0% by weight of fatty acid polyglycol ester (having 40 EO). This mixture is added slowly at room temperature with stirring to 30.0% by weight of an aqueous solution of the sodium salt of a phosphorylated ethylene oxide/propylene oxide/ethylene oxide block copolymer, and the mixture is stirred until the emulsion is homogeneous. 12.0% by weight of the sodium salt of an alkyl polyglycol ether sulfate (wetting agent A) is then added with further stirring, and then 5.0% by weight of propylene glycol, and the white emulsion which has formed is stirred for another 15 minutes (approximately).

What is claimed is:

1. A herbicidal agent which consists of
   a) herbicides selected from the group consisting of leaf-acting selection herbicides and the leaf-acting nonselective herbicides glyphosate, paraquat and diquat;
   b) surfactants selected from the group consisting of $C_{10}$–$C_{18}$-alkyl polyglycol ether sulfates and their physiologically acceptable salts;
   c) optionally, one or more additional insecticides, acaricides, fungicides herbicides, safeners, fertilizers or growth regulators;

d) optionally, a self-emulsifying oil;

e) optionally, one or more non-emulsifying adjuvants.

2. The agent according to claim 1, wherein the ratio by weight of herbicide to surfactant is 10:1 to 1:200.

3. The agent according to claim 1, wherein the adjuvant is a dispersant, penetrant, defoamer, detergent, inert carrier or filler, or a paraffin oil.

4. The agent as claimed in claim 3, wherein the concentration of surfactant in an aqueous spray mixture is 0.05 to 2% by weight of detergent.

5. The agent as claimed in claim 1, wherein the herbicides employed are selective herbicides selected from the group consisting of the grass herbicides, urea derivatives, sulfonylurea herbicides, diphenyl ether derivatives and dicotyledon herbicides.

6. The agent according to claim 1, wherein the leaf-acting selective herbicide is fenoxaprop-ethyl and the surfactant is $Na^+$ $C_{12}/C_{14}$-fatty alcohol diglycol ether sulfate.

7. The agent as claimed in claim 1, wherein the ratio of herbicide to surfactant is 10:1 to 1:200.

8. The agent as claimed in claim 5 wherein the herbicide is phenoxyphenoxy- and heteroaryloxyphenoxypropionic acids and their esters, cyclohexanedione derivatives, wild oat herbicides, isoproturon, chlortoluron, sulfonylureas, diphenyl ether derivatives, hormone herbicides, hydroxybenzonitriles, phenmedipham, diflufenican, fluroxypyr, ethofumesate, quinmerac, quinchlorac, bentazone, metamitron, S-23121 and V-53482.

9. A method for controlling harmful plants, which comprises applying to said plants or to an environment where they reside, a herbicidally effective amount of an agent according to claim 1.

10. The method according to claim 9, wherein the leaf-selective herbicide is fexoxaprop-ethyl and the surfactant is $Na^+$ $C_{12}/C_{14}$-fatty alcohol diglycol ether sulfate.

11. The method as claimed in claim 9, wherein the ratio by weight of herbicide to surfactant is 10:1 to 1:200.

12. The method as claimed in claim 9, wherein the application is carried out by an aqueous spray mixture in which the concentration of surfactant is 0.05 to 2% by weight.

13. The method as claimed in claim 9, wherein the dosage rate of surfactant is 600 to 900 g of detergent per hectare of area under cultivation.

14. The method as claimed in claim 9, wherein the harmful plants are controlled selectively in crops of usefuil plants.

15. In a method for improving the effectiveness of herbicides selected from leaf-acting selective herbicides and the leaf-acting non-selective herbicides glyphosate, paraquat and diquat, the improvement which comprises adding, as the sole surfactant, a surfactant selected form the group consisting of $C_{10}$–$C_{18}$-alkyl polyglycol ether sulfates and their physiologically acceptable salts.

16. The method according to claim 15 wherein the herbicide is selected from the group consisting of the grass herbicides, urea derivatives, sulfonylurea herbicides, diphenyl ether derivatives and dicotyledon herbicides as the herbicides.

* * * * *